(12) United States Patent
Hawkins (10) Patent No.: US 9,770,643 B2
(45) Date of Patent: Sep. 26, 2017

(54) SUPPLEMENT DISPENSING MOUTHGUARD

(71) Applicant: Gretta Hawkins, Castle Rock, CO (US)

(72) Inventor: Victor J. Hawkins, Castle Rock, CO (US)

(73) Assignee: VJ Designs, LLC, Highlands Ranch, CO (US)

( * ) Notice: Subject to any disclaimer, the term of this patent is extended or adjusted under 35 U.S.C. 154(b) by 557 days.

(21) Appl. No.: 13/645,922

(22) Filed: Oct. 5, 2012

(65) Prior Publication Data

US 2013/0087157 A1 Apr. 11, 2013

Related U.S. Application Data

(60) Provisional application No. 61/544,955, filed on Oct. 7, 2011.

(51) Int. Cl.
*A63B 71/08* (2006.01)
*A61C 7/08* (2006.01)
*A61C 19/06* (2006.01)

(52) U.S. Cl.
CPC .............. *A63B 71/085* (2013.01); *A61C 7/08* (2013.01); *A61C 19/06* (2013.01); *A61C 19/063* (2013.01); *A63B 2071/088* (2013.01)

(58) Field of Classification Search
CPC ... A63B 71/085; A63B 2071/085; A61C 7/08; A61C 19/06; A61C 19/063
USPC .................. 128/859, 861, 862; 433/6, 80, 81
See application file for complete search history.

(56) References Cited

U.S. PATENT DOCUMENTS

| | | | | |
|---|---|---|---|---|
| 5,620,011 | A | * | 4/1997 | Flowers ............... B63C 11/186 128/859 |
| 5,842,860 | A | * | 12/1998 | Funt ............................ 433/80 |
| 5,993,413 | A | * | 11/1999 | Aaltonen et al. ........... 604/77 |
| 2011/0027748 | A1 | * | 2/2011 | Fusi et al. .................. 433/80 |
| 2014/0238417 | A1 | | 8/2014 | Turkbas |

OTHER PUBLICATIONS

1987 SafeTGard Product Catalog, Specialized Athletic Protection, pp. 4 and 5.
2007 SafeTGard Product Catalog, Specialized Athletic Protection, pp. 5 and 6.
Hydra-Guard | the World's First Refillable Hydrating Mouth Guard, retrieved Apr. 21, 2015, http://www.hydratingmouthguard.com/#2, 6 pages.

* cited by examiner

*Primary Examiner* — Keri J Nelson
(74) *Attorney, Agent, or Firm* — Holzer Patel Drennan (57) ABSTRACT

The supplement dispensing mouthguards disclosed herein include one or more supplement cavities that store a supplement and one or more openings connected to the supplement cavities. The openings receive the supplement into a mouthguard and discharge the supplement from the mouthguard into a user's mouth. The supplement dispensing mouthguards may be worn during physical activity for protection and/or jaw alignment. Once a desired supplement has filled, been inserted, or placed within the mouthguard, the mouthguard is inserted into the user's mouth and the supplement is gradually and safely dispersed into the user's mouth through openings in the mouthguard.

22 Claims, 9 Drawing Sheets

SUPPLEMENT DISPENSING MOUTHGUARD

CROSS-REFERENCE TO RELATED APPLICATIONS

The present application claims benefit of priority to U.S. Provisional Patent Application No. 61/544,955, entitled "Mouthguard with Supplement Dispensing Cavity" and filed on Oct. 7, 2011, which is specifically incorporated by reference herein for all that it discloses or teaches.

BACKGROUND

A mouthguard (also known as a mouth protector, mouth piece, gumshield, gumguard or nightguard) is a protective device for the mouth that covers the teeth and gums to prevent and reduce injury to the teeth, arches, lips and/or gums. Mouthguards are most often used to prevent injury in contact sports, as a treatment for bruxism or (temporomandibular joint disorder) TMD, or as part of certain dental procedures, such as tooth bleaching.

Mouthguards may be stock (i.e., ready-made), mouth-adapted (e.g., boil-and-bite), or custom made. Stock mouthguards may be manufactured in pre-formed shapes and in various sizes but have limited adjustment (e.g., trimming with a knife or scissors only) to fit a specific user's mouth. Mouth-adapted mouthguards are typically made of a thermo-plastic material (e.g., ethylene-vinyl acetate) manufactured in a pre-formed shape in various sizes. The mouth-adapted mouthguards are then adapted to fit the user's teeth and gums by heating the mouthguard and molding the mouthguard while it is still warm. More specifically, the mouthguard may be placed in boiling water to heat it and then placed in the user's mouth. The user bites down on the mouthguard to form the mouthguard to the user's mouth (including the user's teeth and gums). Custom-made mouthguards are made by taking an impression of a user's mouth and teeth by a specialist manufacturer to create a mouth protector specifically for that user. The impression may be obtained by specifically designed home impression kit from the guard manufacturer that uses dental putty, or from a dentist who will take an upper impression in dental alginate material, for example

SUMMARY

Implementations described and claimed herein address the foregoing problems by providing a supplement dispensing mouthguard that incorporates an area in which a supplement is added to the mouthguard and from which the supplement is distributed to a user wearing the mouthguard.

Other implementations are also described and recited herein.

DETAILED DESCRIPTIONS

FIGS. 1-8 illustrate example implementations of supplement dispensing mouthguards with supplement cavities, example methods of inserting supplements into the supplement cavities, and where/how supplements are dispersed into a user's mouth using the supplement dispensing mouthguards.

The supplement dispensing mouthguards may be worn during physical activity for protection and/or jaw alignment in which the supplements can be inserted for distribution to the during the physical activity. Once a desired supplement has filled, been inserted, or placed within the mouthguard, the mouthguard is inserted into the user's mouth and the supplement is gradually and safely dispersed into the user's mouth through openings in the mouthguard. In one implementation, a combination of the user's saliva and/or water mixing with the supplement allows a gradual dispersing of supplement through openings in the mouthguard.

The openings in the mouthguard allow the supplement to discharge from the mouthguard and absorb easily and quickly into the user's body via the user's mouth. In addition, the openings on the mouthguard, as well as any fill holes or insertion slots, can be placed on a variety of surfaces of the mouthguard (e.g., a buccal, lingual, and/or occlusal surface and openings in the sides, top, inside, front and/or back of the mouthguard). The supplements can be sold in tablets, strips, gels, pastes and/or liquids separately from the mouthguard, so as to extend the product life of the mouthguard and offer a variety of supplements for the user to try and use. The mouthguard may have a variety of styles and include a variety of options (e.g., a top and bottom protective guard, a top only mouthguard, and a mouthguard with or without a tether and/or a breathing hole).

Figure 1:
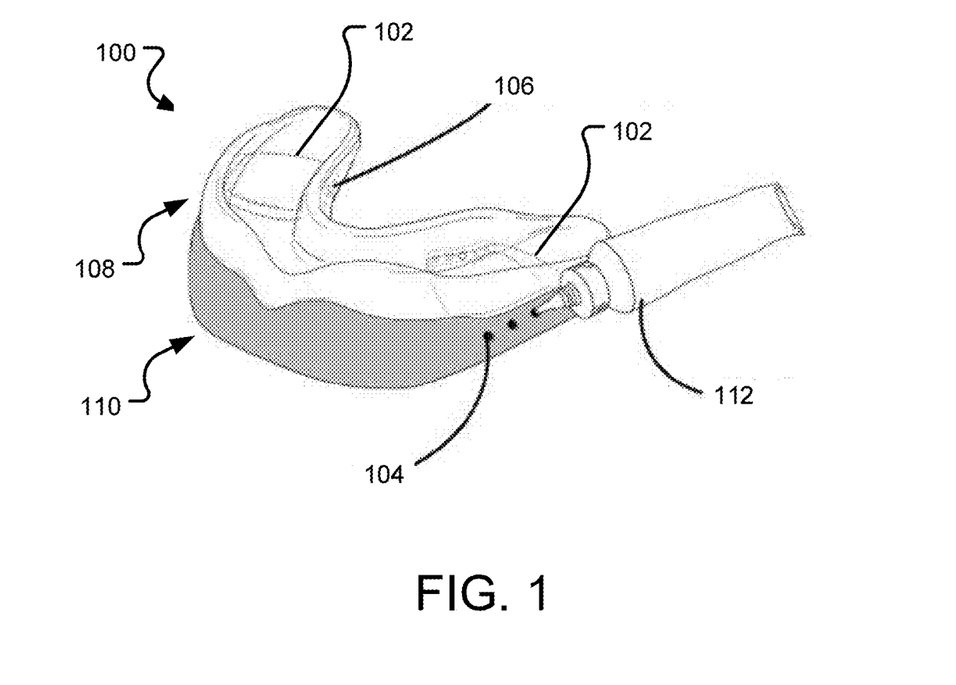
FIG. 1 illustrates a perspective view of an example supplement dispensing mouthguard with supplement cavities, exterior-facing fill holes, and interior-facing dispersion openings.

FIG. 1 illustrates a perspective view of an example supplement dispensing mouthguard 100 with supplement cavities 102, exterior-facing fill holes (e.g., fill hole 104), and interior-facing dispersion openings (e.g., dispersion opening 106). The mouthguard 100 may be stock, mouth-adapted, or custom made as discussed above. Further, the mouthguard 100 may be constructed of a variety of materials (e.g., various plastics, including thermo-set plastics).

The supplement cavities 102 are formed within the mouthguard 100 and are configured to receive various supplements (e.g., flavoring, nutrition, energy, electrolytes, and/or vitamins) in a variety of forms (e.g., solid tablets, strips, powders, gels, pastes, and/or liquids). The supplement cavities 102 may be configured to receive a specific form of supplement or a variety of forms of supplement. For example, the user may squeeze a tube 112 of gel, liquid, or paste supplement through the exterior-facing fill holes into the supplement cavities 102 to fill the supplement cavities 102 with supplement. In one implementation, the exterior-facing fill holes allow the user to refill the supplement cavities 102 while wearing the mouthguard 100. Further, the mouthguard 100 may be equipped with plugs or valves (not shown) to selectively close some of all of the fill holes after the supplement cavities 102 are filled with supplement. The supplement cavities 102 may be various sizes and shapes within the mouthguard 100. Further, there may be one or many supplement cavities within the mouthguard 100.

After the supplement cavities 102 are filled with supplement, the user may insert the mouthguard 100 into his/her mouth (not shown) and orient the his/her upper teeth and gums in an upper tray 108 of the mouthguard 100 and the user's lower teeth and gums in a lower tray 110 of the mouthguard 100. Compressive pressure from the user's jaw and/or form fitting to the user's teeth and/or gums holds the mouthguard 100 in place within the user's mouth. The supplement flows from the supplement cavities 102 into the user's mouth via the interior-facing dispersion openings. This allows the user to receive the supplement while wearing the mouthguard 100 and without occupying the user's hands to ingest the supplement while wearing the mouthguard 100.

The dispersion opening are one or more of round openings, rectangular openings, oval openings, slots and slits. The interior-facing dispersion openings may be sized appropriately to deliver a rate of supplement release from the supplement cavities 102 desirable to the user and the expected duration that the user will wear the mouthguard 100. Further, the user may control the rate of supplement release from the mouthguard 100 by either sucking on the mouthguard 100 or chewing on the mouthguard 100 to increase the rate of supplement discharge. Still further, the mouthguard 100 may be equipped with plugs or valves to selectively close some of all of the dispersion openings to control the rate of supplement discharge into the user's mouth. Further yet, the user's tongue may be used to manipulate valves on the dispersion openings to control the rate of supplement discharge into the user's mouth while the mouthguard 100 is within the user's mouth. Saliva flowing through the dispersion openings and/or fill holes may facilitate the discharge of supplement into the user's mouth.

The dispersion openings may also function as fill holes, and vice-versa. In some implementations, the fill holes and/or dispersion openings may incorporate one-way valves (e.g., diaphragm, swing, and duckbill) (not shown). For example, the user may fill the supplement cavities 102 with the supplement without the supplement flowing back out of the fill holes. Further, the supplement may release out of the dispersion openings without the user's saliva entering the dispersion openings.

Figure 2:
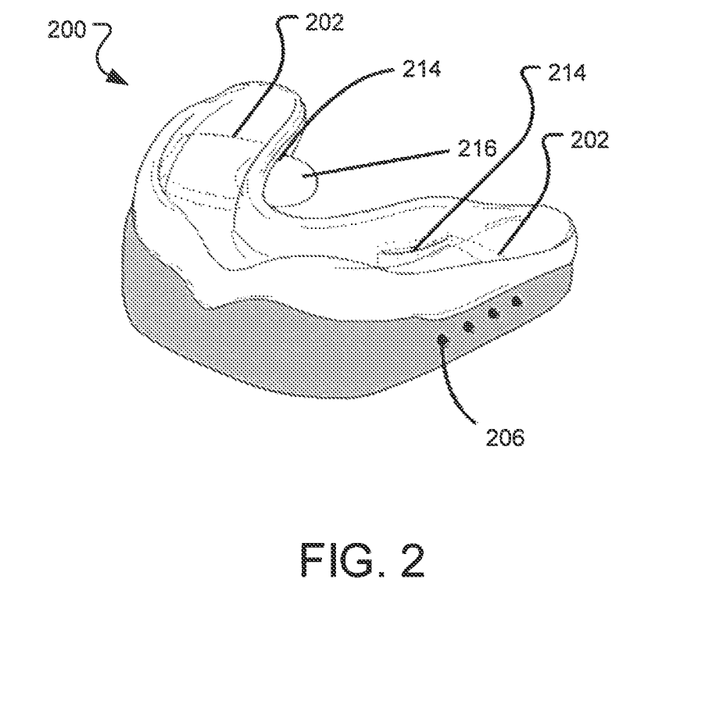
FIG. 2 illustrates a perspective view of an example supplement dispensing mouthguard with supplement cavities, interior-facing insertion slots, and exterior-facing dispersion openings.

FIG. 2 illustrates a perspective view of an example supplement dispensing mouthguard 200 with supplement cavities 202, interior-facing insertion slots 214, and exterior-facing dispersion openings (e.g., opening 206). The supplement cavities 202 are formed within the mouthguard 200 and may receive various supplements in a variety of forms. The supplement cavities 202 may receive a specific form of supplement or a variety of forms of supplement. For example, the user may insert a supplement tablet 216 through one or both of the interior-facing insertion slots 214 and into one or both of the supplement cavities 202 to fill the supplement cavities 202 with supplement. The supplement tablet 216 may be a solid tablet or a powder, gel or liquid filled dissolvable capsule or packet, for example. The supplement cavities 202 may be various sizes and shapes within the mouthguard 200. Further, there may be one or many supplement cavities within the mouthguard 200.

After the supplement cavities 202 are filled with supplement, the user may insert the mouthguard 200 into his/her mouth (not shown) and supplement flows from the supplement cavities 202 into the user's mouth via the dispersion openings 206 and/or the insertion slots 214. The dispersion openings 206 may be sized appropriately to deliver a rate of supplement release from the supplement cavities 202 desirable to the user and the expected duration that the user will wear the mouthguard 200. Saliva flowing through the dispersion openings 206 and/or insertion slots 214 may facilitate the discharge of supplement into the user's mouth. In some implementations, the dispersion openings 206 are not included and the supplement exclusively disperses from the insertion slots 214.

The dispersion openings 206 may also function as fill holes for optional insertion of supplement via a tube (e.g., tube 112 of FIG. 1). Further, the insertion slots 214 may act as one-way valves by allowing the user to fill one or both of the supplement cavities 202 with the supplement tablet 216 without the supplement tablet 216 readily falling out of one or both of the supplement cavities 202.

Figure 3:
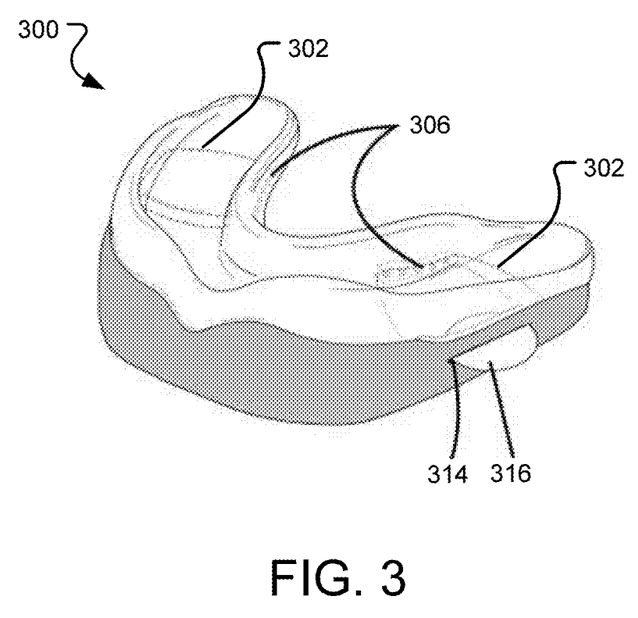
FIG. 3 illustrates a perspective view of an example supplement dispensing mouthguard with supplement cavities, exterior-facing insertion slots, and interior-facing dispersion openings.

FIG. 3 illustrates a perspective view of an example supplement dispensing mouthguard 300 with supplement cavities 302, exterior-facing insertion slots (e.g., insertion slot 314), and interior-facing dispersion openings (e.g., openings 306). The supplement cavities 302 are formed within the mouthguard 300 and may receive various supplements in a variety of forms. The supplement cavities 302 may receive a specific form of supplement or a variety of forms of supplement. For example, the user may insert a supplement tablet 316 through one or both of the exterior-facing insertion slots and into one or both of the supplement cavities 302 to fill the supplement cavity with supplement. In one implementation, the exterior-facing insertion slots allow the user to refill the supplement cavities 302 while wearing the mouthguard 300. The supplement cavities 302 may be various sizes and shapes within the mouthguard 300. Further, there may be one or many supplement cavities within the mouthguard 300.

After the supplement cavities 302 are filled with supplement, the user may insert the mouthguard 300 into his/her mouth (not shown) and supplement flows from the supplement cavities 302 into the user's mouth via the dispersion openings and/or the insertion slots. The dispersion openings may be sized appropriately to deliver a rate of supplement release from the supplement cavities 302 desirable to the user and the expected duration that the user will wear the mouthguard 300. Saliva flowing through the dispersion openings and/or insertion slots may facilitate discharge of the supplement into the user's mouth.

The dispersion openings may also function as fill holes for optional insertion of the supplement via a tube (e.g., tube 112 of FIG. 1). Further, the insertion slots may act as one-way valves by allowing the user to fill one or both of the supplement cavities 302 with the supplement tablet 316 without the supplement tablet 316 readily falling out of one or both of the supplement cavities 302.

Figure 4:
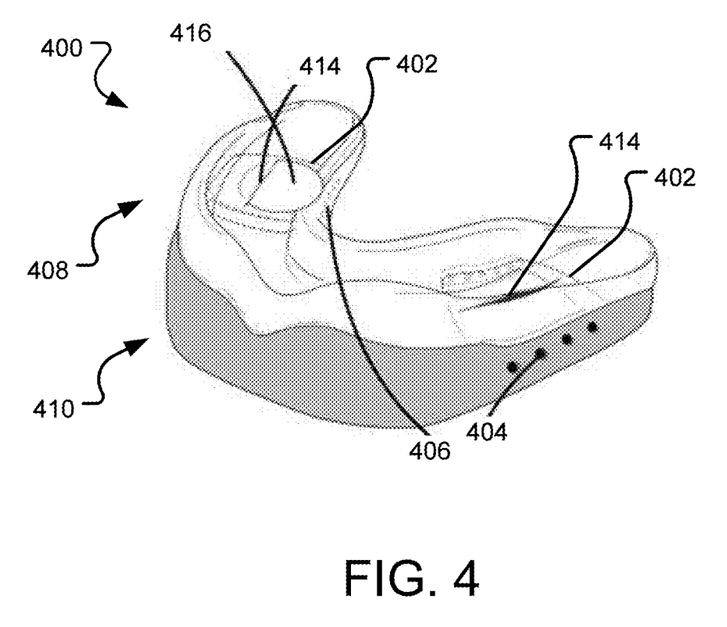
FIG. 4 illustrates a perspective view of an example supplement dispensing mouthguard with supplement cavities, top-facing insertion slots, interior-facing openings, and exterior-facing openings.

FIG. 4 illustrates a perspective view of an example supplement dispensing mouthguard 400 with supplement cavities 402, top-facing insertion slots 414, interior-facing openings (e.g., opening 406), and exterior-facing openings (e.g., opening 404). The top-facing insertion slots 414 open into an upper tray 408 of the mouthguard 400. In other implementations, the insertion slots 414 face downward and open into a lower tray 410 of the mouthguard 400. In some implementations, a user squeezes the mouthguard 400 to selectively open the insertion slots 414. When the user releases the mouthguard 400, the insertion slots 414 substantially close.

The supplement cavities 402 are formed within the mouthguard 400 and may receive various supplements in a variety of forms. The supplement cavities 402 may receive a specific form of supplement or a variety of forms of supplement. For example, the user may insert a supplement tablet 416 through one or both of the top-facing insertion slots 414 and into one or both of the supplement cavities 402 to fill the supplement cavities 402 with supplement. The supplement cavities 402 may be various sizes and shapes within the mouthguard 400. Further, there may be one or many supplement cavities within the mouthguard 400.

After the supplement cavities 402 are filled with supplement, the user may insert the mouthguard 400 into his/her mouth (not shown) and supplement flows from the supplement cavities 402 into the user's mouth via the openings and/or the insertion slots 414. The dispersion openings may be sized appropriately to deliver a rate of supplement release from the supplement cavities 402 desirable to the user and the expected duration that the user will wear the mouthguard 400. Saliva flowing through the openings and/or insertion slots may facilitate the discharge of supplement into the user's mouth. Having both interior-facing openings (e.g., opening 406) and exterior-facing openings (e.g., opening 404) may facilitate the flow of saliva through the supplement cavities 402 and/or the supplement out of the supplement cavities 402.

The openings may also function as fill holes for optional insertion of supplement via a tube (e.g., tube 112 of FIG. 1). Further, the insertion slots 414 may act as one-way valves by allowing the user to fill one or both of the supplement cavities 402 with the supplement tablet 416 without the supplement tablet 416 readily falling out of one or both of the supplement cavities 402.

Figure 5A:
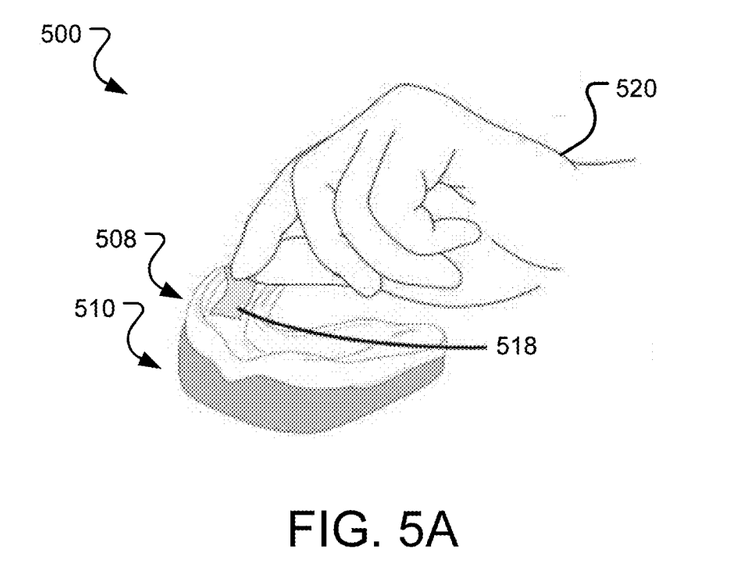
FIG. 5A illustrates a perspective view of an example supplement dispensing mouthguard with a user installing a supplement strip.

FIG. 5A illustrates a perspective view of an example supplement dispensing mouthguard 500 with a user 520 installing a supplement strip 518. The user 520 orients the supplement strip 518 over an upper tray 608 of the mouthguard 500. The supplement strip 518 may be sticky and thus naturally adhere to the mouthguard 500 or the user may wet the supplement strip 518 to provide adhesion to the mouthguard 500. In this manner, the user 520 may install multiple supplement strips on the upper tray 508 or a lower tray 510 of the mouthguard 500. The supplement strip 518 may be used in addition or in lieu of the supplement cavities also discussed herein.

Figure 5B:
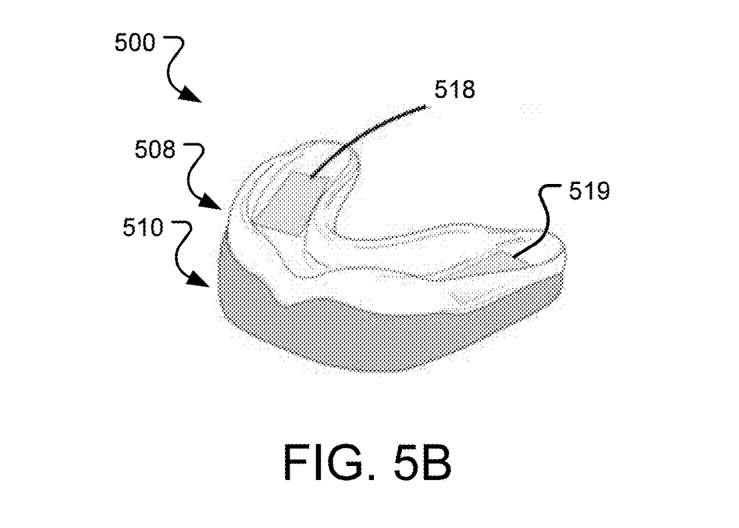
FIG. 5B illustrates the supplement dispensing mouthguard of FIG. 5A with two supplement strips installed in the upper tray of the mouthguard.

FIG. 5B illustrates the supplement dispensing mouthguard 500 of FIG. 5A with two supplement strips 518, 519 installed in the upper tray 508 of the mouthguard 500. The supplement strips 518, 519 may stick to the mouthguard 500 and/or be secured adjacent the mouthguard 500 with compressive pressure from the user's jaw while the mouthguard 500 is within the user's mouth. The user's saliva will initiate and/or facilitate dissolving the supplement strips 518, 519 and thus release the supplement within the user's mouth. The surface area and composition of the supplement strips 518, 519 may be selected so that the supplement strips 518, 519 dissolve within a desired timeframe and/or release supplement at a desired rate. In other implementations, one or more supplement strips are instead or also installed in the lower tray 510 of the mouthguard 500. The supplement strips 518 may be used in addition or in lieu of the supplement cavities also discussed herein.

Figure 6:
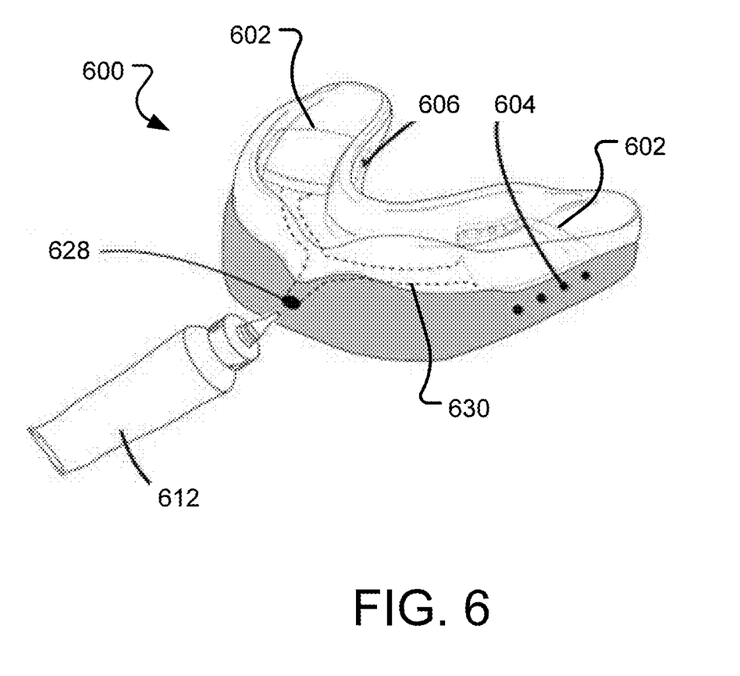
FIG. 6 illustrates a perspective view of an example supplement dispensing mouthguard with supplement cavities, a front-facing fill hole, interior-facing dispersion openings, and exterior-facing dispersion openings.

FIG. 6 illustrates a perspective view of an example supplement dispensing mouthguard 600 with supplement cavities 602, a front-facing fill hole 628, interior-facing dispersion openings (e.g., opening 606), and exterior-facing dispersion openings (e.g., opening 604). The supplement cavities 602 are formed within the mouthguard 600 and may receive various supplements in a variety of forms. The supplement cavities 602 may receive a specific form of supplement or a variety of forms of supplement.

For example, the user may squeeze a tube 612 of gel, liquid, or paste supplement through the fill hole 628. The supplement travels through interior passages (e.g., passage 630) into the supplement cavities 602 to fill the supplement cavities 602 with supplement. The fill hole 628 connects to both supplement cavities 602 to allow a user to fill both supplement cavities 602 via the one fill hole 628 and the interior passages. Further, in one implementation, the fill hole 628 allows the user to refill the supplement cavities 602 while wearing the mouthguard 600. Further, the mouthguard 600 may be equipped with plugs or valves (not shown) to selectively close the fill hole 628 after the supplement cavities 602 are filled with supplement. The supplement cavities 602 may be various sizes and shapes within the mouthguard 600. Further, there may be one or many supplement cavities within the mouthguard 600.

After the supplement cavities 602 are filled with supplement, the user may insert the mouthguard 600 into his/her mouth (not shown) and the supplement flows from the supplement cavities 602 into the user's mouth via the openings. The openings may be sized appropriately to deliver a rate of supplement release from the supplement cavities 602 desirable to the user and the expected duration that the user will wear the mouthguard 600. Further, the mouthguard 600 may be equipped with plugs or valves to selectively close some of all of the openings to control the rate of supplement discharge into the user's mouth. Saliva flowing through the openings may facilitate the discharge of supplement into the user's mouth. Having both interior-facing openings (e.g., opening 606) and exterior-facing dispersion openings (e.g., opening 604) may facilitate the flow of saliva through the supplement cavities 602 and/or supplement out of the supplement cavities 602. One or more of the interior-facing and exterior-facing openings may also function to fill the cavities 602 with supplement. In some implementations, the openings may incorporate one-way valves (e.g., diaphragm, swing, and duckbill) (not shown).

Figure 7:
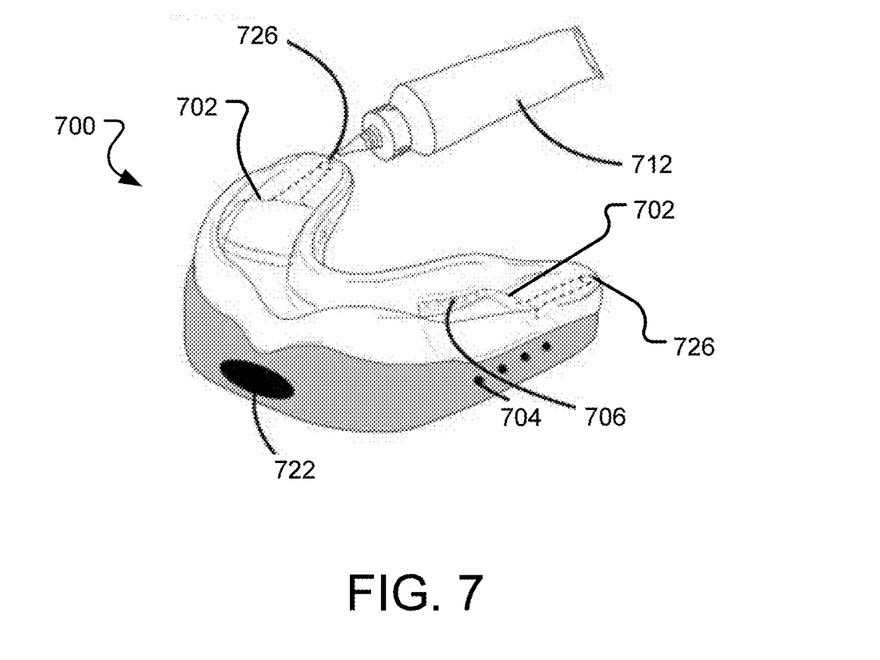
FIG. 7 illustrates a perspective view of an example supplement dispensing mouthguard with supplement cavities, rear-facing fill holes, interior-facing dispersion openings, and exterior-facing dispersion openings.

FIG. 7 illustrates a perspective view of an example supplement dispensing mouthguard 700 with supplement cavities 702, rear-facing fill holes 726, interior-facing dispersion openings (e.g., opening 706), and exterior-facing dispersion openings (e.g., opening 704). The supplement cavities 702 are formed within the mouthguard 700 and may receive various supplements in a variety of forms. The supplement cavities 702 may receive a specific form of supplement or a variety of forms of supplement. For example, the user may squeeze a tube 712 of gel, liquid, or paste supplement through the fill holes 726 into the supplement cavities 702 to fill the supplement cavities 702 with supplement. Further, the mouthguard 700 may be equipped with plugs or valves (not shown) to selectively close some of all of the fill holes 726 after the supplement cavities 702 are filled with supplement. The supplement cavities 702 may be various sizes and shapes within the mouthguard 700. Further, there may be one or many supplement cavities within the mouthguard 700.

After the supplement cavities 702 are filled with supplement, the user may insert the mouthguard 700 into his/her mouth (not shown) and supplement flows from the supplement cavities 702 into the user's mouth via the openings. The openings may be sized appropriately to deliver a rate of supplement release from the supplement cavities 702 desirable to the user and the expected duration that the user will wear the mouthguard 700. Further, the mouthguard 700 may be equipped with plugs or valves to selectively close some or all of the openings 706 to control the rate of supplement discharged into the user's mouth. Saliva flowing through the openings may facilitate the discharge of supplement into the user's mouth. Having both interior-facing openings (e.g., opening 706) and exterior-facing dispersion openings (e.g., opening 704) may facilitate the flow of saliva through the supplement cavities 702 and/or supplement out of the supplement cavities 702. The dispersion openings may also function as fill holes, and vice-versa. In some implementations, the openings may incorporate one-way valves (e.g., diaphragm, swing, and duckbill) (not shown).

The mouthguard 700 also includes a breathing vent 722 oriented at a front of the mouthguard 700. The breathing vent 722 helps a user breathe via the user's mouth while wearing the mouthguard 700. In some implementations, the breathing vent 722 is omitted.

Figure 8:
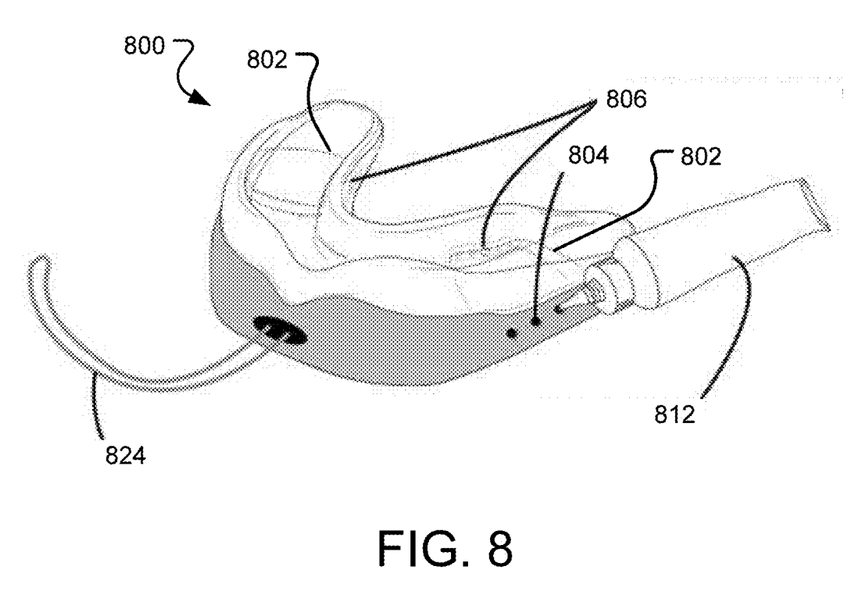
FIG. 8 illustrates a perspective view of an example supplement dispensing mouthguard with supplement cavities, fill holes, dispersion openings, and a tether.

FIG. 8 illustrates a perspective view of an example supplement dispensing mouthguard 800 with supplement cavities 802, fill holes (e.g., fill hole 804), dispersion openings (e.g., dispersion opening 806), and a tether 824. The supplement cavities 702 are formed within the mouthguard 700 and may receive various supplements in a variety of forms. The supplement cavities 802 may receive a specific form of supplement or a variety of forms of supplement. For example, the user may squeeze a tube 812 of gel, liquid, or paste supplement through the fill holes into the supplement cavities 802 to fill the supplement cavities 802 with supplement.

After the supplement cavities 802 are filled with supplement, the user may insert the mouthguard 800 into his/her mouth (not shown) and the supplement flows from the supplement cavities 802 into the user's mouth via the dispersion openings. The tether 824 allows the user to attach the mouthguard 800 to the user's helmet (not shown) or other personal equipment. As a result, when the mouthguard 800 is removed from the user's mouth, the mouthguard 800 is still attached to the user for quick retrieval.

Figure 9:
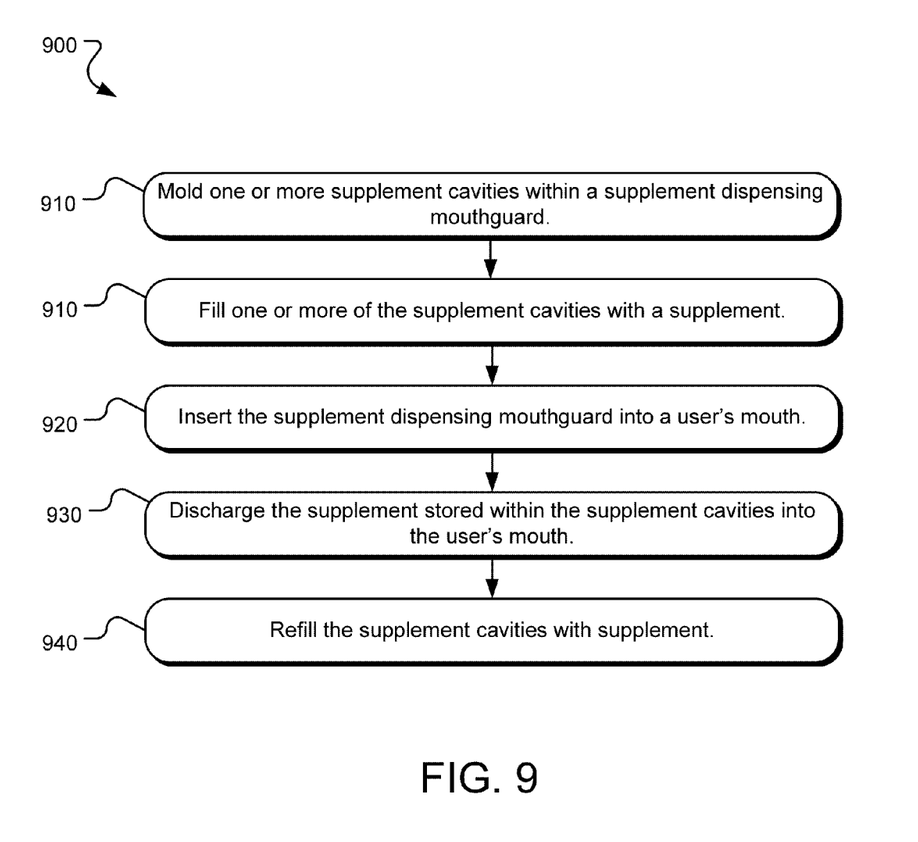
FIG. 9 illustrates a method of making and using a supplement dispensing mouthguard.

FIG. 9 illustrates a method 900 of making and using a supplement dispensing mouthguard. A molding operation 910 molds one or more supplement cavities within a supplement dispensing mouthguard. The molding operation 910 may occur at a factory and use a variety of molding techniques (e.g., blow-molding, compression-molding, injection-molding, laminating, thermoforming, etc.). The mouthguard is also molded with one or more holes, slots, or other openings that allow a user to fill the supplement cavities with supplement and that discharge the supplement from the supplement cavities at a desired rate. In another implementation, an inseration slot may be cut, rather than molded, in the mouthguard.

A filling operation 920 fills one or more of the supplement cavities with a supplement. In various implementations, the filling operation 920 is accomplished by placing a nozzle of a supplement tube containing a liquid or semi-liquid supplement over an opening leading to a supplement cavity. The user squeezes the tube thereby pushing the supplement into the supplement cavity and substantially filling the supplement cavity with supplement. In another implementation, the supplement is a solid that may be pressed through a slit on the supplement cavity and secured within the supplement cavity behind the slit. The supplement provides the user with dispensed and orally ingested or absorbed flavoring, nutrition, energy, electrolytes, and/or vitamins, for example.

An insertion operation 920 inserts the supplement dispensing mouthguard into the user's mouth prior to discharging the supplement. A discharging operation 930 discharges the supplement stored within the supplement cavities into the user's mouth as the user wears the mouthguard. The discharging operation 930 may be configured to deliver the supplement to the user's mouth at a desired rate. Further, the user may vary the rate of discharge by sucking or chewing on the mouthpiece.

A refilling operation 940 may refill the supplement cavities with supplement. The refilling operation may be accomplished is a manner similar to filling operation 910. Further, refilling operation 940 may be accomplished while the mouthguard is within the user's mouth or after removing the mouthguard from the user's mouth.

The embodiments of the invention described herein are implemented as logical steps. Accordingly, the logical operations making up the embodiments of the invention described herein are referred to variously as operations, steps, objects, or modules. Furthermore, it should be understood that logical operations may be performed in any order, with additional operations and/or deleted operations, unless explicitly claimed otherwise or a specific order is inherently necessitated by the claim language.

The above specification, examples, and data provide a complete description of the structure and use of exemplary embodiments of the invention. Since many embodiments of the invention can be made without departing from the spirit and scope of the invention, the invention resides in the claims hereinafter appended. Furthermore, structural features of the different embodiments may be combined in yet another embodiment without departing from the recited claims.

What is claimed is:

1. An apparatus comprising:
   a supplement dispensing mouthguard, including:
   a supplement cavity molded within the mouthguard, the supplement cavity configured to be disposed adjacent an occlusal surface of a user's teeth when worn, the supplement cavity further configured to store a supplement within the mouthguard;
   one or more fill holes located on a first surface of the mouthguard, connected to the supplement cavity, and configured to receive the supplement into the supplement cavity of the mouthguard; and
   one or more dispersion openings on a second surface of the mouthguard, the dispersion openings opposing the one or more fill holes and configured to discharge the supplement from the supplement cavity within the mouthguard.

2. The apparatus of claim 1, further comprising:
an insertion slot on a surface of the mouthguard and connected to the supplement cavity and configured to receive the supplement into the supplement cavity of the mouthguard.

3. The apparatus of claim 2, wherein the insertion slot is top-facing.

4. The apparatus of claim 1, wherein the supplement contains one or more of energy, electrolytes, vitamins, and flavoring.

5. The apparatus of claim 1, wherein the supplement is one of a gel, a liquid, a paste, a solid tablet, and a strip.

6. The apparatus of claim 1, wherein the one or more dispersion openings are located in one or more of a rear surface, a front surface, an inside surface, an outside surface, a top surface, and a bottom surface of the mouthguard.

7. The apparatus of claim 1, further comprising:
a second supplement cavity configured to store a second supplement within the mouthguard; and
one or more dispersion openings on a surface of the mouthguard and connected to the second supplement cavity configured to discharge the second supplement from the mouthguard.

8. The apparatus of claim 1, wherein the supplement dissolves within the mouthguard when exposed to one or both of water and a user's saliva.

9. The apparatus of claim 1, wherein the one or more dispersion openings are sized to discharge the supplement into a user's mouth at a desired rate.

10. The apparatus of claim 1, wherein the one or more dispersion openings are one or more of round openings, rectangular openings, oval openings, slots, and slits.

11. The apparatus of claim 1, wherein the supplement cavity has any volume-enclosing shape.

12. The apparatus of claim 1, wherein the one or more fill holes are located on one of a lingual surface and a buccal surface of the mouthguard and the one or more dispersion openings are located on one of the opposite of the lingual surface and the buccal surface of the fill holes of the mouthguard.

13. A method of manufacturing a mouthguard comprising:
molding a supplement dispensing mouthguard, including:
molding one or more supplement cavities configured to be located adjacent an occlusal surface of a user's teeth, one or more fill holes in the mouthguard, and one or more dispersion openings in the mouthguard, wherein the one or more supplement cavities are configured to store a supplement within the mouthguard, wherein the one or more fill holes in the mouthguard are located on a first surface of the mouthguard, wherein the one or more fill holes are connected to the one or more supplement cavities and configured to receive the supplement into the one or more supplement cavities of the mouthguard, wherein the one or more dispersion openings are located on a second surface of the mouthguard opposing the first surface of the one or more fill holes and wherein the one or more dispersion openings are connected to the one or more supplement cavities and configured to discharge the supplement from within the mouthguard.

14. The method of claim 13, further comprising:
cutting an insertion slot in the mouthguard, wherein the insertion slot is connected to the one or more supplement cavities and configured to receive the supplement into the one or more supplement cavities of the mouthguard.

15. The method of claim 13, wherein the one or more dispersion openings are located in one or more of a rear surface, a front surface, an inside surface, an outside surface, a top surface, and a bottom surface of the mouthguard.

16. The method of claim 13, wherein the one or more dispersion openings are sized to discharge the supplement into a user's mouth at a desired rate.

17. The method of claim 13, wherein the one or more dispersion openings are one or more of round openings, rectangular openings, oval openings, slots, and slits.

18. The method of claim 13, wherein the one or more fill holes are located on one of a lingual surface and a buccal surface of the mouthguard and the one or more dispersion openings are located on one of the opposite of the lingual surface and the buccal surface of the fill holes of the mouthguard.

19. A method of using a supplement dispensing mouthguard comprising:
placing the supplement dispensing mouthguard within a user's mouth, the mouthguard including a supplement cavity configured to be disposed adjacent an occlusal surface of the user's teeth when worn;
filling the supplement cavity with a supplement via one or more fill holes on a first surface of the mouthguard and connected to the supplement cavity configured to receive the supplement into the supplement cavity of the mouthguard;
dissolving the supplement within the mouthguard when exposed to one or both of water and a user's saliva; and
discharging the supplement stored within the supplement cavity of the mouthguard into the user's mouth through one or more dispersion openings located on a second surface of the mouthguard opposite the one or more fill holes as the user wears the mouthguard.

20. The method of claim 19 further comprising:
inserting the mouthguard into the user's mouth prior to discharging the supplement.

21. The method of claim 19, further comprising:
filling a second supplement cavity formed within the mouthguard with a second supplement; and
discharging the second supplement stored within the second supplement cavity of the mouthguard into the user's mouth as the user wears the mouthguard.

22. The method of claim 19, wherein there are two or more dispersion openings and the two or more dispersion openings are located on two or more of rear surface, a front surface, an inside surface, an outside surface, a to surface, and a bottom surface of the mouthguard.

\* \* \* \* \*

UNITED STATES PATENT AND TRADEMARK OFFICE
CERTIFICATE OF CORRECTION

PATENT NO. : 9,770,643 B2
APPLICATION NO. : 13/645922
DATED : September 26, 2017
INVENTOR(S) : Victor J. Hawkins It is certified that error appears in the above-identified patent and that said Letters Patent is hereby corrected as shown below:

In the Claims

Column 9, Line 2, of Claim 2 recites:
"an insertion slot on a surface of the mouthguard and".
Should recite:
"wherein the one or more fill holes are insertion slots on a surface of the mouthguard and".

Column 9, Line 14, of Claim 6 recites:
"dispersion openings are located in one or more of a rear".
Should recite:
"dispersion openings fill holes are located in one or more of a rear".

Column 9, Lines 19-23, of Claim 7 recites:
"supplement within the mouthguard; and one or more dispersion openings on a surface of the mouthguard and connected to the second supplement cavity configured to discharge the second supplement from the mouthguard".
Should recite:
"supplement within the mouthguard and disposed adjacent another occlusal surface of the user's teeth.".

Column 10, Line 11, of Claim 15 recites:
"dispersion openings are located in one or more of a rear".
Should recite:
"dispersion openings fill holes are located in one or more of a rear".

Column 10, Line 49, of Claim 21 recites:
"mouthguard with a second supplement; and".
Should recite:
"mouthguard with a second supplement via a second set of one or more fill holes located on the first surface of the mouthguard; and".

Signed and Sealed this
Twelfth Day of June, 2018

Andrei Iancu
*Director of the United States Patent and Trademark Office*

CERTIFICATE OF CORRECTION (continued)
U.S. Pat. No. 9,770,643 B2

Column 10, Line 52, of Claim 21 recites:
"user's mouth as the user wears the mouthguard.".
Should recite:
"user's mouth as the user wears the mouthguard via a second set of one or more dispersion openings located on the second surface of the mouthguard, the second surface of the mouthguard opposing the first surface of the mouthguard.".